United States Patent
Wu et al.

(10) Patent No.: US 6,420,307 B1
(45) Date of Patent: Jul. 16, 2002

(54) FLUIDIZED-BED CATALYST FOR PROPYLENE AMMOXIDATION TO ACRYLONITRILE

(75) Inventors: Lianghua Wu; Guojun Wang; Xin Chen, all of Shanghai (CN)

(73) Assignee: China Petro-Chemical Corporation (CN)

( * ) Notice: Subject to any disclaimer, the term of this patent is extended or adjusted under 35 U.S.C. 154(b) by 0 days.

(21) Appl. No.: 09/642,289

(22) Filed: Aug. 18, 2000

(30) Foreign Application Priority Data

Aug. 19, 1999 (CN) ......................................... 99113987 A
Aug. 19, 1999 (CN) ......................................... 99113988 A
Aug. 19, 1999 (CN) ......................................... 99113989 A
Nov. 3, 1999 (CN) ......................................... 99119953 A

(51) Int. Cl.$^7$ ............................. B01J 23/00; B01J 21/08; B01J 21/12; B01J 21/14

(52) U.S. Cl. ........................ 502/300; 502/240; 502/241; 502/242; 502/243; 502/244; 502/245; 502/246; 502/247; 502/248; 502/250; 502/252; 502/253; 502/254; 502/258; 502/263; 502/300; 502/302

(58) Field of Search ............................. 502/240–260, 502/263, 305–355

(56) References Cited

U.S. PATENT DOCUMENTS

| | | | | |
|---|---|---|---|---|
| 4,863,891 A | * | 9/1989 | Grasselli et al. ............ | 502/306 |
| 5,093,299 A | * | 3/1992 | Suresh et al. ................ | 502/212 |
| 5,223,469 A | * | 6/1993 | Chen et al. .................. | 502/209 |
| 5,491,258 A | * | 2/1996 | Watanabe et al. ............ | 562/538 |
| 5,532,199 A | * | 7/1996 | Watanabe et al. ........... | 502/311 |
| 5,834,394 A | * | 11/1998 | Chen et al. .................. | 502/306 |
| 5,840,648 A | * | 11/1998 | Suresh et al. ................ | 502/306 |
| 6,143,690 A | * | 11/2000 | Komada et al. ............. | 502/211 |

* cited by examiner

Primary Examiner—Mark L. Bell
Assistant Examiner—Patricia L. Hailey
(74) Attorney, Agent, or Firm—Anderson Kill & Olick, P.C.

(57) ABSTRACT

The present invention relates to a new fluidized-bed catalyst used in a process of propylene ammoxidation to acrylonitrile. The catalyst comprises a silica as carrier and a composition represented by the following general formulas:

$$A_aB_bC_cGe_dNa_eFe_fBi_gMo_hO_x$$

Wherein

A represents at least one element selected from a group consisting Li,K,Rb,Cs,Sm, In or Tl;

B represents at least one element selected from a group consisting of P, Sb, Cr, W. Pr, Ce, As, B, Te, Ga, Al, Nb, Th, La or V;

C represents one element selected from a group consisting of Ni, Co, Sr, Mn, Mg, Ca, Zn, Cd or Cu and the mixture thereof;

a is a number of from 0.01 to 1.5;

b is a number of from 0.01 to 3.0;

c is a number of from 0.1 to 12.0; preferably from 2 to 10;

d is a number of from 0.01 to 2.0; preferably from 0.01 to 1.0;

e is a number of from 0.01 to 0.7; preferably from 0.05 to 0.5;

f is a number of from 0.1 to 8; preferably from 1.0 to 3.0;

g is a number of from 0.01 to 6; preferably from 0.1 to 2.0;

h is a number of from 12 to 14.5;

X denotes the number of oxygen atoms which satisfies the valence requirement of the other elements in the catalyst;

The content of silica used as carrier is, 30–70 wt %.

The catalyst of the invention can be used in the reaction for propylene ammoxidation to acrylonitrile operated at a higher reaction pressure and higher load condition, and can still sustain a high once-through yield of acrylonitrile.

11 Claims, No Drawings

FLUIDIZED-BED CATALYST FOR PROPYLENE AMMOXIDATION TO ACRYLONITRILE

FIELD OF THE INVENTION

The present invention relates to a catalyst for propylene ammoxidation to acrylonitrile. More particularly, the present invention relates to a fluidized-bed catalyst for propylene ammoxidation to acrylonitrile.

BACKGROUND OF THE INVENTION

The acrylonitrile is a basic organic chemical material. It has been widely used in chemical industry. At present, producing acrylonitrile mainly use the process of propylene ammoxidation. In the process, catalyst makes important effect on propylene conversion, acrylonitrile selectivity, and so on. Nowadays, the most popular catalyst used for the propylene ammoxidation is a fluidized-bed catalyst. In order to get high activity and high selectivity. The catalyst have already been made a series of improvements through long-lasting research. Most of these improvements mainly focused on the active component of the catalyst and the mixture ratio of the active component.

It has been well know that the balance between acrylonitrile output and market demand is gradually being formed. Nowadays, acrylonitrile manufacturers are paying more attention to increasing acrylonitrile output and reducing starting material consumption of existing plants rather than setting up new plants. Utilizing a new catalyst with excellent performance replace old one to innovate existing plant can eliminate the so called "bottle neck" in the production process, increase 50–80% production capacity and save lots of cost in comparison with setting up new plant. The economic efficiency is considerable high.

However, two problems will occur in the process of making technical innovation. One is reaction pressure go up, another is catalyst amount is beyond a certain limitation. Therefore, it is required that the new catalyst should have higher capacity for loading propylene and higher capacity for bearing reaction pressure.

The reaction pressure of fluidized-bed reactor comes from a series of equipment resistance from the outlet of reactor to the top of absorbing tower, such as heat exchanger, tower and pipeline. Because of increasing production capacity, it consequently makes the amount of flowing materials apparently increase at reactor outlet and results in the increase of resistance. In addition, it makes further increase of resistance force that more heat exchanging equipment need to be used due to the deficient heat transferring area. In order to meet the requirement of the environmental protection, the waste gas of reaction from the absorbing tower top is not allowed to discharge directly into atmosphere and it will be transferred to waste-gas burning unit to burn. Thus, the pressure of the top of absorbing tower is to be raised if a blowing machine has not been used. Due to the above-mentioned reasons, at present, the running pressure of reactor is higher than the design pressure by 0.5–1.0 times. It is to reach up to above 0.08 Mpa.

Actually, the second problem is a catalyst load, namely WWH. It means the weight of proprlene feed per unit weight of catalyst per hour. With increase of the feedstock entered into the reactor, the fluidizing height of catalyst may exceed the height of cooling water pipe if the catalyst load is unchanged. At the same time, the reaction linear velocity of the reactor also should be outstandingly raised. These two changes may lead the increase of reactor dilute phase temperature, resulting in the increase of the amount of carbon dioxide formed and the decrease of the acrylonitrile selectivity. Accordingly, the catalyst with higher WWH can settle the above-mentioned problem.

Theoretically, the capacity of absorbing propylene should be improved as the increase of the catalyst WWH. However, there is not any theory indicate a certain relationship between the metal elements used in the catalyst and capacity of absorbing propylene.

Various methods were proposed in the prior art for solving the aforementioned problems. For example, Chinese patent CN1021638C disclosed the catalyst, which had a composition represented by following general formula:

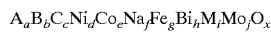

Wherein,

A represents K, Rb, Cs, Sm and Tl;

B represents Mn, Mg, Sr, Ca, Ba, La and rare earth element;

C represents P, As, B, Sb and Cr

M represents W, V

The catalyst had a higher yield of acrylonitrile, but lower propylene load. The yield of acrylonitrile of the said catalyst would be considerably decreased under higher reaction pressure. Based upon further research done by the present inventor, it is found that the component B and M have effect on the running load of the catalyst and on its properties under high pressure. Some metal elements of component B will adversely affects on the increase of running load of catalyst as well as the catalyst properties under high pressure, so these metals are not suitable to be used in the catalyst running under higher pressure and higher load. Besides, in the above-mentioned Chinese patent CN1021638C, it was provided that the sum of i and j in the catalyst composition should be 12, namely it was a constant. Under the rule, the component Mo was decreased as the component M was increased. It would result in the adverse effect on the acrylonitrile yield. The catalyst composition of the present invention is not limited by the rule.

DETAILED DESCRIPTION OF THE INVENTION

The object of the present invention is to provide a new fluidized-bed catalyst for propylene ammoxidation to acrylonitrile, which can overcome the problem that the fluidized-bed catalyst for propylene ammoxidation to acrylonitrile is not suitable for higher reaction pressure and higher load. The catalyst of the present invention can achieve higher acrylonitrile even under higher reaction pressure and higher load.

The object of the present invention can be realized by a new fluidized-bed catalyst is used in the process of propylene ammoxidation to crylonitrile. The catalyst comprises silica as carrier and a catalytic composition represented by following general formula:

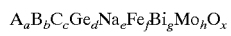

Wherein component A represents at least one element selected from the group consisting of Li, K, Rb, Cs, Sm, In and Tl;

component B represents a mixture of Pr plus W or a mixture of Pr plus W and at least one element selected from the group consisting of P, Sb, Cr, Ce, As, B, Te, Ga, Al, Nb, Tb, La and V;

component C represents at least one element selected from the group consisting of Ni, Co, Sr, Mn, Mg, Ca, Zn, Cd, Cu and mixtures thereof;

a is a number of from 0.01 to 1.5;

b is a number of from 0.01 to 3.0;

c is a number of from 0.1 to 12.0; preferably from 2 to 10;

d is a number of from 0.01 to 2.0; preferably from 0.01 to 1.0;

e is a number of from 0.01 to 0.7; preferably from 0.05 to 0.5;

f is a number of from 0.1 to 8; preferably from 1.0 to 3.0;

g is a number of from 0.01 to 6; preferably from 0.1 to 2.0;

h is a number of from 12 to 14.5;

the atom value of Pr is a number of from 0.01 to 0.75;

the atom value of W is a number of from 0.01 to 1.0; and x is a number of oxygen atoms required to satisfy the valence requirement of the other element in the catalyst;

The content of silica as carrier is 30–70 wt %; preferable 40–60 wt %.

In a preferred embodiment of the invention, the component C is selected from the group consisting of Mg and a mixture of Mg with other metals. In another preferred embodiment of the invention, the component B is selected from the group consisting of a mixture of Pr plus W plus Sb and a mixture of Pr plus W plus Sb with other metals, and component C is selected from the group consisting of Sr and a mixture of Sr with other metals. In another preferred embodiment of the invention, component B is selected from the group consisting of a mixture of Pr plus W plus Ce and a mixture of Pr plus W plus Ce with other metals, and component C is selected from the group consisting of Mg and a mixture of Mg with other metals. In another preferred embodiment of the invention, component B is selected from the group consisting of Pr plus W plus Cr plus La and a mixture of Pr plus W plus Cr plus La with other metals, and component C is selected from the group consisting of Mg and a mixture of Mg with other metals.

The fluidized-bed catalyst of the present invention is named as Mo—Bi type catalyst because Mo and Bi constitute the main active components in this type of catalyst. Fe can form various new compounds by mixing it with Mo—Bi, so as to make the catalyst have higher activity and selectivity. Besides, it can not only speed up to reach the balance of oxidation-reduction reaction of the catalyst and maintain the stability of the catalyst structure, but also prevent Mo—Bi system from being permanently deactivated under the condition of low oxygen.

In the catalyst of the invention, A type of metals are mainly used for lessening the surface acidity of the catalyst and enhancing the selectivity of propylene ammoxidation to acrylonitrile. The B type of metals are added as an assistant component of active phase in the catalyst and they usually form a structure of heteropolyacid salt with active component. The C type of metals is mainly used as promoter. They can make the catalyst have a proper oxidation capability so as to prevent the reaction from excessive oxidation, therefore the catalyst performances of both activity and selectivity can be enhanced.

In the present invention, Na added into the catalyst can not only strengthen resistance attrition, but also enhance both the activity and selectivity when Na is used together with Ge.

There is no special requirement on the process of preparing the catalyst of the invention. The catalyst of the invention may be prepared by various conventional methods. The preparing process may comprises: the selected components are mixed to form a solution, then mixed with catalyst carrier to obtain a slurry, the resultant slurry is spray dried to solid particles and calcined to obtain the catalyst. The aforementioned slurry is preferably prepared with the process described in Chinese patent CN1005248C. The said process is as follows: the various components of the catalyst in the form of aqueous solution and the carrier are added into the equipment for manufacturing catalyst in the order as indicated in the below mentioned examples of the present invention. Alternatively, some of the components are premixed with Mo compound to form molybdate, then mixed with other components. Due to the excellent resistance of the catalysts to attrition, it is not necessary for the carrier to be added into the catalyst of the invention by multiple times. So preparation of the catalyst is greatly simplified.

The starting materials used for preparing the catalyst of the invention may be selected by a manner as follows:

Mo component as the starting material used for preparing the catalyst can be selected from a group consisting of molybdnum oxide, ammonium molybdate or molybdnum salts.

Na component as the starting material used for preparing the catalyst can be selected from a group consisting of sodium nitrate, sodium hydroxide, sodium silicate or any decomposable Na compound. There is no special requirement on the order of adding Na component into the slurry. Na component can be added into the solution of ammonium molybdate, the solution of nitrate or into the ammonia-stabilized silica sol used as carrier. Alternatively, Na component also can be added into ammonia-stabilized silica sol in the plant for manufacturing silica sol in advance by requiring the manufacturer of silica sol to do so. If such is the case, the weight ratio of $SiO_2/Na_2O$ should be within the range from 150 to 550, preferably from 200 to 400.

To introduce into the catalyst, one preferably employs respectively the acids of P, As and B or the ammonium salts thereof. To introduce W into the catalyst, one can employ ammonium tungstate or tungsten oxide. To introduce V into the catalyst, one can employ ammonium metavanadate. To introduce Ge into the catalyst, one can employ the oxides of Ge. To introduce Cr into the catalyst, one preferably employs chromium trioxide, chromium nitrate or the mixture thereof. To introduce Sb into the catalyst, one can employ antimony trioxide, antimony pentoxide and antimony halide or antimony sol which can be hydrolyzed to form antimony oxide. To introduce Ce, Pr, Rb, La and Tb into the catalyst, one can employ nitrate or salts, which can be decomposed to form oxides thereof.

To introduce into the catalyst, one can respectively employ the oxides of Bi, Fe and Sr or the salts thereof which can be decomposed to oxides, most preferably employs water soluble nitrates. To introduce rest of metal components other than aforementioned elements into the catalyst, one can employ nitrates of these metals, oxides thereof or salts thereof which can be decomposed to oxides, most preferably employs water soluble nitrates thereof.

In the method for preparing the catalyst of the invention, the compounded slurry is heated and concentrated till the solid content reaching to 47–55 wt %, then spray dried. The spray drier used in the method can be one selected from a group consisting of pressure-type, parallel flow type or centrifugal rotating-disc drier, preferably is the centrifugal rotating-disc drier which can ensure the catalyst prepared have a good distribution of size.

Calcination of the catalyst can be divided into two steps i.e. the decomposition of the salts of various elements in the catalyst and the calcination at high temperature. Temperature for decomposition is preferably 200–300° C., the time for calcination is from 20 minutes to two hours. The decomposition and calcination can be carried out respectively in two calcinators. It is also possible that a calcinator is divided to two sections respectively for decomposition and calcination, or the decomposition and calcination are carried out in a continuous rotating calcinator. A certain amount of air should be introduced into the process of decomposition and calcination of the catalyst to prevent the catalyst from being reduced excessively.

Propylene, ammonia and molecular oxygen employed in the process of producing acrylonitrile by using the catalyst of the invention is same as that employed in the ammoxidation process by using other catalyst. Although, the content of low molecular saturated hydrocarbon in propylene as raw material will have no effect on the reaction, the concentration of propylene is preferably more than 85% (mole) from the point of view of economics and safety. The ammonia used can be liquid ammonia with fertilizer grade. The molecular oxygen required for reaction can be pure oxygen, oxygen rich air or normal air, while preferably is normal air from the point of view of economics and safety.

The molar ratio of ammonia to propylene as feedstock added into the fluidized-bed reactor is within the range from 0.8 to 1.5, preferably from 1.0 to 1.3. The molar ratio of air to propylene is within the range from 8 to 10.5, preferably from 9.0 to 9.8. The molar ratio of air to propylene also can be up to 11 if it is required due to some reasons in the running and there is still no any adverse effect on the reaction. However, the amount of excessive oxygen in the reaction gas had better be no more than 7% (volume) by taking the consideration of safety, preferably no more than 4% (volume).

When the catalysts of the present invention are used in a fluidized-bed reactor, the reaction temperature is 420–470° C., preferably 425–450° C. The catalyst of the present invention is suitable for running under the condition of high-pressure, high-load. Hence, the reaction pressure in the production unit can be up to over 0.08 Mpa, for example, 0.08–0.15 Mpa. If the reaction pressure is below 0.08 Mpa, there is no any disadvantageous effect on the reaction while the yield of acrylonitrile can be increased further.

The propylene load of the catalyst of the invention (WWH) is 0.06–0.15 $hr^{-1}$, preferably 0.07–0.1 $hr^{-1}$. If the load is too low, it will not only cause the waste of catalyst, but also increases the amount of carbon dioxide formed and decreases the selectivity. If the load is too high, it has not practical value. It is the amount of catalyst is so little that make the transferring heat area of cooling water tube in the catalyst layer is less than the area required to remove the reaction heat. As a result, the reaction temperature will be out of control.

THE BEST MODE FOR CARRYING OUT THE PRESENT INVENTION

The evaluation of the activity of the catalyst of the present invention is determined using a fluidized-bed reactor having an inner diameter of 38 mm. The amount of the catalyst provided to the reactor is 440–550 g, the reaction temperature is 430–440° C., the reaction pressure is 0.14 Mpa, the molar ratio of propylene to ammonia to air in the feedstock is 1:1.2:9.5–9.8, the propylene load of the catalyst (WWH) is 0.085–0.090 $hr^{-1}$.

The propylene conversion and the selectivity of acrylonitrile and the yield of acylonitrile are respectively calculated in accordance with the following equations.

$$\text{propylene conversion (\%)} = \frac{\text{moles of propylene converted}}{\text{moles of propylene fed}} \times 100\%$$

$$\text{acrylonitrile selectivity (\%)} = \frac{\text{moles of acrylonitrile produced}}{\text{moles of propylene converted}} \times 100\%$$

once-through yield of acrylonitrile (%) =

$$\frac{\text{moles of acrylonitrile produced}}{\text{moles of propylene fed}} \times 100\%$$

The content of silica in the catalyst is 40–60 wt %.

The following non-limiting examples will serve to illustrate the present invention in more details. However, it should be understood that these examples are only illustrative and should in no way limit the scope of the present invention. It will be apparent that numerous variations, modifications, and alternative embodiments are to be regarded as being within the spirit and scope of the present invention as claimed.

EXAMPLE 1

The catalyst with the composition of $Mo_{12}Bi_{1.0}Fe_{2.0}Co_{2.5}Ni_{5.5}K_{0.1}Cs_{0.05}Cr_{0.5}Pr_{0.3}Ge_{0.05}Na_{0.29}O_x$ 1.8 g of cesium nitrate, 4.64 g sodium nitrate were mixed with 1.87 g of potassium nitrate, the resultant mixture then was heated and dissolved in 30 g of water to form feedstock (A). 9.34 g of chromium trioxide was dissolved in 8.4 g of water to form feedstock (B). 395.2 g of ammonium molybdate was dissolved in 325 g of hot water at a temperature of 50–90° C. to form feedstock (C). 90.45 g of bismuth nitrate, 135.6 of cobalt nitrate, 14.7 g of praseodymium nitrate, 0.97 g of germanium oxide, 298.38 of nickel nitrate were mixed with 150.8 g of ferric nitrate, 70 g of water was added into the resultant mixture, then dissolved while heating to form feedstock (D).

The feedstock (A) was mixed with 1250 g of 40 wt % silica sol. The feedstock (B), (C) and (D) were added into the resultant mixture while stirring. After thoroughly stirring, the slurry thereby was formed. The resultant slurry was formed into solid particles in the spray drier by a conventional method, and finally was calcined at 610° C. for 1 hour in a rotating calcinator having an inner diameter of 89 mm and a length of 1700 mm to obtain a catalyst having the following composition: $Mo_{12}B_{1.0}Fe_{2.0}Co_{2.5}Ni_{5.5}K_{0.1}Cs_{0.05}Cr_{0.5}Pr_{0.3}Ge_{0.05}Na_{0.29}O_x$+50% $SiO_2$.

EXAMPLES 2–9

Comparative Examples 1–4

The same process as described in Example 1 was employed to obtain various catalysts with different compositions as indicated in the following Table 1. The all catalysts thus obtained and above-mentioned catalyst was employed in the reaction of propylene ammoxidaton to acrylonitrile under the reaction conditions setting out below to evaluate the property of the said catalysts. The results are shown in Table 1.

In the above-mentioned examples and the comparative examples thereafter, the reaction conditions employed were as follows:

| | |
|---|---|
| fluidized-bed reactor having an inner diameter of 38 mm | |
| reaction temperature | 440° C. |
| reaction pressure | 0.14 Mpa |
| filling amount of catalyst | 550 g |
| propylene load of catalyst (WWH) | 0.090 hr$^{-1}$ |
| mixture ratio (mole) of the feedstock | propylene/NH3/air = 1/1.2/9.8 | solid particles, then calcined at 605° C. for 1.5 hr in a rotating calcinator having an inner diameter of 89 mm and a length of 1700 mm to thereby obtain a catalyst. The catalyst obtained had a composition as follows: 50%$K_{0.1}Na_{0.28}Cs_{0.07}P_{0.025}Ni_{5.6}Cr_{0.35}Ce_{0.35}Mg_{1.2}Ge_{0.05}Fe_{2.0}Bi_{0.75}Mo_{12.5}O_x$+50%$SiO_2$,

EXAMPLES 11–17

Comparative Examples 5–8

According to the process as described in Example 1, the catalysts having different compositions as indicated in Table

TABLE 1

| Example | Catalyst Composition | Acrylonitrile Yield, % | Acrylonitrile Selectivity, % | Propylene Conversion, % |
|---|---|---|---|---|
| Example 1 | $Mo_{12}Bi_{1.0}Fe_{2.0}Co_{2.5}Ni_{5.5}K_{0.1}Cs_{0.05}Cr_{0.5}Pr_{0.3}Ge_{0.05}Na_{0.29}O_x$ | 80.6 | 81.7 | 98.7 |
| Example 2 | $Mo_{12}Bi_{1.0}Fe_{2.0}Co_{2.5}Ni_{5.5}K_{0.07}Cs_{0.08}Cr_{0.8}Ge_{0.5}Na_{0.29}Sb_{0.5}O_x$ | 81.4 | 82.1 | 99.2 |
| Example 3 | $Mo_{12}Bi_{1.0}Fe_{2.5}Co_{1.5}Ni_{6.0}K_{0.15}Cs_{0.05}Ge_{0.5}Na_{0.29}W_{1.0}P_{0.25}O_x$ | 80.0 | 81.2 | 98.5 |
| Example 4 | $Mo_{12}Bi_{1.0}Fe_{1.5}Ni_{7.0}Cs_{0.1}Pr_{0.3}Ge_{0.2}Na_{0.29}W_{0.8}Sb_{0.5}O_x$ | 79.8 | 81.5 | 97.9 |
| Example 5 | $Mo_{12}Bi_{1.0}Fe_{2.0}Co_{5.0}Ni_{2.5}K_{0.05}Cs_{0.2}Cr_{0.5}Ge_{0.5}Na_{0.29}V_{0.5}P_{0.50}$ | 81.1 | 82.2 | 98.7 |
| Example 6 | $Mo_{12}Bi_{1.0}Fe_{2.5}Co_{2.5}Ni_{6.0}K_{0.05}Cs_{0.2}Tl_{0.05}Pr_{0.3}Ge_{0.3}Na_{0.29}Sb_{0.5}O_x$ | 80.9 | 81.8 | 98.9 |
| Example 7 | $Mo_{12}Bi_{1.0}Fe_{1.5}Co_{2.5}Ni_{6.0}Cs_{0.2}Tl_{0.25}Cr_{0.45}Pr_{0.3}Ge_{0.03}Na_{0.29}P_{0.5}O_x$ | 79.5 | 81.0 | 98.1 |
| Example 8 | $Mo_{12}Bi_{1.0}Fe_{2.0}Co_{2.0}Ni_{7.0}K_{0.09}Cs_{0.05}Tl_{0.25}Ge_{0.03}Na_{0.29}W_{0.1}V_{0.3}Sb_{0.5}O_x$ | 82.3 | 82.9 | 99.3 |
| Example 9 | $Mo_{12}Bi_{1.0}Fe_{2.5}Co_{2.5}Ni_{6.5}K_{0.13}Cs_{0.08}Cr_{0.5}Pr_{0.3}Ge_{0.5}Na_{0.29}W_{0.5}Sb_{0.5}O_x$ | 80.7 | 81.5 | 99.0 |
| Comparative 1 | $Mo_{12}Bi_{0.9}Fe_{1.8}Ni_{2.0}Co_{5.0}Na_{0.15}Mn_{0.45}Cr_{0.45}K_{0.17}Cs_{0.05}O_x$ | 76.8 | | |
| Comparative 2 | $Mo_{12}Bi_{0.9}Fe_{1.8}Ni_{2.0}Co_{5.0}Na_{0.15}Mn_{0.45}Cr_{0.45}K_{0.21}O_x$ | 76.2 | | |
| Comparative 3 | $Mo_{12}Bi_{0.9}Fe_{1.8}Ni_{2.4}Co_{4.3}Na_{0.15}W_{0.45}Cr_{0.45}K_{0.15}Cs_{0.07}O_x$ | 77.1 | | |
| Comparative 4 | $Mo_{12}Bi_{0.9}Fe_{1.8}Ni_{5.0}Mg_{2.0}Na_{0.15}W_{0.45}Cr_{0.45}Cs_{0.09}O_x$ | 77.4 | | |

TABLE 2

| Example | Catalyst Composition | Acrylonitrile Yield, % | Acrylonitrile Selectivity, % | Propylene Conversion, % |
|---|---|---|---|---|
| Example 10 | $K_{0.1}Na_{0.28}Cs_{0.07}P_{0.025}Ni_{5.6}Cr_{0.35}Ce_{0.35}Mg_{1.2}Ge_{0.05}Fe_{2.0}Bi_{0.75}Mo_{12.5}O_x$ | 80.5 | 81.9 | 98.3 |
| Example 11 | $K_{0.1}Na_{0.28}Cs_{0.07}P_{0.03}Co_{4.5}Cr_{0.35}W_{0.12}Ce_{0.35}Mg_{1.2}Ge_{0.075}Fe_{2.0}Bi_{0.75}Mo_{12.5}O_x$ | 79.9 | 81.5 | 98.0 |
| Example 12 | $K_{0.1}Na_{0.28}Cs_{0.07}P_{0.03}Ni_{5.6}Mn_{0.1}W_{0.12}Ce_{0.45}Mg_{1.2}Ge_{0.05}Fe_{2.0}Bi_{0.75}Mo_{12.5}O_x$ | 80.0 | 81.8 | 97.8 |
| Example 13 | $K_{0.1}Na_{0.28}Cs_{0.07}As_{0.05}Ni_{5.6}Cr_{0.45}Ce_{0.50}Mg_{1.5}Ge_{0.05}Fe_{2.0}Bi_{0.75}Mo_{12.5}O_x$ | 79.7 | 81.7 | 97.6 |
| Example 14 | $K_{0.1}Na_{0.28}Cs_{0.07}As_{0.05}Ni_{5.6}W_{0.12}Ce_{0.30}Mg_{1.2}Ge_{0.075}Fe_{2.0}Bi_{0.75}Mo_{12.5}O_x$ | 79.6 | 81.1 | 98.2 |
| Example 15 | $K_{0.14}Cs_{0.07}As_{0.05}V_{2.0}Cr_{0.4}Mn_{0.1}W_{0.12}Ce_{0.25}Mg_{1.2}Ge_{0.075}Fe_{2.5}Bi_{0.75}Mo_{12.5}O_x$ | 80.1 | 81.2 | 98.6 |
| Example 16 | $K_{0.14}Cs_{0.07}P_{0.025}V_{2.0}Cr_{0.45}W_{0.14}Ce_{0.35}Mg_{1.2}Ge_{0.035}Fe_{2.0}Bi_{1.0}Mo_{12.5}O_x$ | 79.7 | 81.0 | 98.4 |
| Example 17 | $K_{0.1}Na_{0.28}Cs_{0.07}P_{0.025}V_{2.0}Cr_{0.4}Cu_{0.15}Ce_{0.35}Mg_{1.2}Ge_{0.05}Fe_{2.0}Bi_{0.75}Mo_{12.5}O_x$ | 79.5 | 81.1 | 98.0 |
| Comparative 5 | $Mo_{12}Bi_{0.9}Fe_{1.8}Ni_{2.0}Co_{5.0}Na_{0.15}Mn_{0.45}Cr_{0.45}K_{0.17}Cs_{0.05}O_x$ | 76.3 | | |
| Comparative 6 | $Mo_{12}Bi_{0.9}Fe_{1.8}Ni_{2.4}Co_{4.3}Na_{0.15}W_{0.45}Cr_{0.45}K_{0.15}Cs_{0.07}O_x$ | 76.5 | | |
| Comparative 7 | $Mo_{12}Bi_{0.9}Fe_{1.8}Ni_{2.0}Co_{5.0}Na_{0.15}Mn_{0.45}Cr_{0.45}K_{0.21}O_x$ | 75.7 | | |
| Comparative 8 | $Mo_{12}Bi_{0.9}Fe_{1.8}Ni_{5.0}Mg_{2.0}Na_{0.15}W_{0.45}Cr_{0.45}Cs_{0.09}O_x$ | 76.9 | | |

EXAMPLE 10

The catalyst contained a composition of $K_{0.1}Na_{0.28}Cs_{0.07}P_{0.025}Ni_{5.6}Cr_{0.35}Ce_{0.35}Mg_{1.2}Ge_{0.05}Fe_{2.0}Bi_{0.75}Mo_{12.5}O_x$.2.1 g of cesium nitrate, 4.35 g of sodium nitrate were mixed with 1.91 g of potassium nitrate, then the resultant mixture was dissolved in 30 g of water while heating to form feedstock (A). 8.37 g of chromium trioxide was dissolved in 9 g of water to form feedstock (B). 421.3 g of ammonium molybdate was dissolved in 350 g of water at a temperature of 60–90° C. to form feedstock (C). 87.2 g of bismuth nitrate, 292 g of nickel nitrate, 50.4 g of cerium nitrate, 102 g of magnesium nitrate, 1.27 g of germanium oxide were mixed with 168 g of ferric nitrate, then the resultant mixture was dissolved in 120 g of water while heating to form feedstock (D). 4.01 g of phosphoric acid solution was used as feedstock (E).

The feedstock (A) was mixed with 1285 g of 40 wt % silica sol. The feedstock (B), (C), (D) and (E) were added in order into the resultant mixture while stirring. After thoroughly stirring, a slurry thereby was obtained. The slurry thus obtained was fed to spray-drying apparatus to form 2 were obtained. Using the catalysts thus obtained, a reaction of propylene ammoxidation to acrylonitrile was conducted under the below mentioned reaction conditions. The results are shown in Table 2.

In the above-mentioned examples and comparative examples, the reaction conditions were as follows, fluidized-bed reactor having an inner diameter of 38 mm reaction temperature 430° C.

reaction pressure 0.14 Mpa, filling amount of catalyst 400 g, propylene load of catalyst (WWH) 0.085 hr$^{-1}$, mixture ratio (mole) of the feedstock propylene/NH3/air= 1/1.2/9.5

EXAMPLE 18

The catalyst contained a composition of $Mo_{12}Bi_{1.0}Fe_{2.0}W_{1.0}Pr_{0.75}Na_{0.3}Ni_{6.0}Mn_{2.0}Ga_{0.1}Cr_{0.75}Ge_{0.5}K_{0.1}Cs_{0.05}Tl_{0.15}O_i$. 0.72 g of Cesium nitrate, 4.8 g of sodium nitrate were mixed with 2.43 g of potassium nitrate. The resultant mixture was dissolved in 30 g of water while heating to obtain feedstock (A). 18.67 g of chromium trioxide was dissolved in 8.4 g of water to obtain feedstock (B). 19.4 g of ammonium tungstate was dissolved in 100 ml 5 wt % aqueous solution of ammonia to obtain a solution. 395.2 g of ammonium molybdate was dissolved in 325 g of hot water at the temperature of 50–90° C. to obtain another solution. These two solutions thus obtained were mixed to thereby obtain feedstock (C). 90.4 g of bismuth, 4.94 g of thallium oxide, 3.29 g of gallium, 65.87 g of manganese nitrate, 2.45 g of praseodymium nitrate, 434 g of nickel nitrate were mixed with 150.8 g ferric nitrate. The resultant mixture was dissolved in 70 g of water while heating to thereby obtain feedstock (D).

Feedstock (A) was mixed with 1250 g of 40 wt % silica sol. Feedstock (B), (C) and (D) were added into the resultant mixture thus obtained. After thoroughly stirring, the slurry was obtained. The slurry thus obtained was fed to a spray-drying apparatus to form solid particles, then calcined at 630° C. for 1 hr in a rotating calcinator having an inner diameter of 89 mm and a length of 1700 mm to thereby obtain a catalyst. The catalyst thus obtained had a composition as follows: 50% $Mo_{12}Bi_{1.0}Fe_{2.0}W_{1.0}Pr_{0.75}Na_{0.3}Ni_{6.0}Mn_{2.0}Ga_{0.1}Cr_{0.75}Ge_{0.5}K_{0.1}Cs_{0.05}Tl_{0.15}O_t$+50%$SiO_2$.

EXAMPLES 19–26

Comparative Examples 9–12

According to the process as described in Example 1, the catalysts having different compositions as indicated in Table 3 were obtained. Using the catalyst thus obtained, a reaction of propylene ammoxidation to acrylonitrile was conducted under the below mentioned reaction conditions. The results are shown in Table 3.

In the above-mentioned embodiment and comparative examples, the reaction conditions were as follows:

| | |
|---|---|
| fluidized-bed reactor having an inner diameter of 38 mm | |
| reaction temperature | 440° C. |
| reaction pressure | 0.14 Mpa |
| filling amount of catalyst | 550 g |
| propylene load of catalyst (WWH) | 0.090 hr$^{-1}$ |
| mixture ratio (mole) of the feedstock | propylene/NH3/air = 1/1.2/9.8 |

EXAMPLE 27

The catalyst contained a composition of $Mo_{12}Bi_{1.0}Fe_{2.0}Sb_{0.3}Sr_{0.2}Na_{0.29}Ni_{5.8}Mg_{2.5}Ge_{0.05}K_{0.08}Cs_{0.05}O_x$. According to the process as described in Example 1, the catalyst having the composition of 50%$Mo_{12}Bi_{1.0}Fe_{2.0}Sb_{0.3}Sr_{0.2}Na_{0.29}Ni_{5.8}Mg_{2.5}Ge_{0.05}K_{0.08}Cs_{0.05}O_x$+50%$SiO_2$ was obtained. Using the catalyst thus obtained, the reaction of propylene ammoxidation to acrylonitrile was conducted at the substantially same conditions as in Example 1. The results thus obtained were as follows:

The acrylonitrile yield was 80.7%. The selectivity of acrylonitrile was 81.5%. The propylene conversion was 99.0%.

EXAMPLE 28

The catalyst contained a composition of $Mo_{12.5}Bi_{0.75}Fe_{2.0}Mg_{1.5}Ge_{0.05}Ce_{0.5}Cr_{0.45}As_{0.1}Na_{0.28}Ni_{5.6}K_{0.01}Cs_{0.07}O_x$. According to the process as described in Example 1, the catalyst having the composition of 50% $Mo_{12.5}Bi_{0.75}Fe_{2.0}Mg_{1.5}Ge_{0.5}Ce_{0.5}Cr_{0.45}As_{0.1}Na_{0.28}Ni_{5.6}K_{0.1}Cs_{0.07}O_x$+50%$SiO_2$ was obtained. Using the catalyst thus obtained, the reaction of propylene ammoxidation to acrylonitrile was conducted at the substantially same conditions as in Example 1. The results thus obtained were as follows:

The acrylonitrile yield was 79.9%. The selectivity of acrylonitrile was 81.7%. The propylene conversion was 97.8%.

EXAMPLE 29

The catalyst contained a composition of $Mo_{12.5}Bi_{0.75}Fe_{2.0}Mg_{1.2}Cu_{0.5}Cr_{0.4}V_{2.0}P_{0.025}K_{0.1}Cs_{0.07}Na_{0.29}Ge_{0.05}O_x$. According to the process as described in Example 1, the catalyst having the composition of 50% $Mo_{12.5}Bi_{0.75}Fe_{2.0}Mg_{1.2}Cu_{0.5}Cr_{0.4}V_{2.0}P_{0.025}K_{0.1}Cs_{0.07}Na_{0.29}Ge_{0.05}O_x$+50% $SiO_2$ was obtained. Using the catalyst thus obtained, the reaction of propylene ammoxidation to acrylonitrile was conducted at the substantially same conditions as in Example 1. The results thus obtained were as follows:

The acrylonitrile yield was 80.6%. The selectivity of acrylonitrile was 81.6%. The propylene conversion was 98.6%.

EXAMPLE 30

The catalyst contained a composition of $Mo_{13}Bi_{1.0}Fe_{2.5}Mg_{2.5}La_{0.45}Cr_{0.55}Mn_{0.15}Ni_{5.0}P_{0.05}Cs_{0.05}K_{0.15}Na_{0.20}Ge_{0.05}O_x$.

TABLE 3

| Example | Catalyst Composition | Acrylonitrile Yield, % |
|---|---|---|
| Example 18 | $Mo_{12}Bi_{1.0}Fe_{2.0}W_{1.0}Pr_{0.75}Na_{0.3}Ni_{6.0}Mn_{2.0}Ga_{0.1}Cr_{0.75}Ge_{0.5}K_{0.1}Cs_{0.05}Tl_{0.15}O_x$ | 81.9 |
| Example 19 | $Mo_{12}Bi_{1.0}Fe_{2.0}W_{0.45}Pr_{0.05}Na_{0.3}Ni_{8.0}Cr_{1.0}Nb_{0.2}K_{0.13}Cs_{0.02}O_x$ | 80.3 |
| Example 20 | $Mo_{12}Bi_{1.0}Fe_{2.0}W_{0.45}Pr_{0.1}Na_{0.3}Ni_{8.0}Cr_{0.5}Ga_{0.5}K_{0.05}Cs_{0.05}Tl_{0.05}O_x$ | 81.4 |
| Example 21 | $Mo_{12}Bi_{1.0}Fe_{2.0}W_{0.75}Pr_{0.2}Na_{0.3}Ni_{8.0}Ge_{0.05}Al_{0.5}Cs_{0.15}Tl_{0.05}O_x$ | 80.0 |
| Example 22 | $Mo_{12}Bi_{1.0}Fe_{2.0}W_{0.75}Pr_{0.25}Na_{0.3}Ni_{6.0}Mn_{2.0}Ge_{0.1}Cr_{1.0}K_{0.08}Cs_{0.12}O_x$ | 79.9 |
| Example 23 | $Mo_{12}Bi_{1.0}Fe_{2.0}W_{0.75}Pr_{0.15}Na_{0.3}Ni_{8.0}Cr_{0.5}Ge_{0.08}K_{0.15}Rb_{0.08}Tl_{0.12}O_x$ | 80.7 |
| Example 24 | $Mo_{12}Bi_{1.0}Fe_{2.0}W_{0.48}Pr_{0.2}Na_{0.3}Ni_{8.0}Nb_{0.1}Cr_{0.8}Ge_{0.2}Rb_{0.05}Cs_{0.15}Tl_{0.05}O_x$ | 79.5 |
| Example 25 | $Mo_{12}Bi_{1.0}Fe_{2.0}W_{0.45}Pr_{0.5}Na_{0.3}Ni_{6.0}Ca_{2.0}Cr_{0.5}Ge_{0.5}K_{0.08}Cs_{0.05}Tl_{0.15}O_x$ | 82.0 |
| Example 26 | $Mo_{12}Bi_{1.0}Fe_{2.0}W_{0.1}Pr_{0.1}Na_{0.3}Ni_{6.0}Ca_{2.0}Cr_{0.8}Ga_{0.1}K_{0.1}Rb_{0.05}Cs_{0.03}O_x$ | 80.5 |
| Comparative 9 | $Mo_{12}Bi_{0.9}Fe_{1.8}Ni_{2.0}Co_{5.0}Na_{0.15}Mn_{0.45}Cr_{0.45}K_{0.17}Cs_{0.05}O_x$ | 76.8 |
| Comparative 10 | $Mo_{12}Bi_{0.9}Fe_{1.8}Ni_{2.0}Co_{5.0}Na_{0.15}Mn_{0.45}Cr_{0.45}K_{0.21}O_x$ | 76.2 |
| Comparative 11 | $Mo_{12}Bi_{0.9}Fe_{1.8}Ni_{2.4}Co_{4.3}Na_{0.15}W_{0.45}Cr_{0.45}K_{0.15}Cs_{0.07}O_x$ | 77.1 |
| Comparative 12 | $Mo_{12}Bi_{0.9}Fe_{1.8}Ni_{5.0}Mg_{2.0}Na_{0.15}W_{0.45}Cr_{0.45}Cs_{0.09}O_x$ | 77.4 |

According to the process as described in Example 1, the catalyst having the composition of 50% $Mo_{13}Bi_{1.0}Fe_{2.5}Mg_{2.5}La_{0.45}Cr_{0.55}Mn_{0.15}Ni_{5.0}P_{0.05}Cs_{0.05}$ $K_{0.15}Na_{0.20}Ge_{0.05}O_x$+50%$SiO_2$ was obtained. Using the catalyst thus obtained, the reaction of propylene ammoxidation to acrylonitrile was conducted at the substantially same conditions as in Example 1. The results thus obtained were as follows:

The acrylonitrile yield was 80.6%. The selectivity of acrylonitrile was 82.0%. The propylene conversion was 98.3%.

EXAMPLE 31

The catalyst contained a composition of $Mo_{13}Bi_{1.0}Fe_{2.5}Mg_{2.5}La_{0.45}Cr_{0.55}Mn_{0.15}Ni_{2.5}Co_{1.5}Cs_{0.05}$ $K_{0.15}Na_{0.20}Ge_{0.05}O_x$. According to the process as described in Example 1, the catalyst having the composition of 50% $Mo_{13}Bi_{1.0}Fe_{2.5}Mg_{2.5}La_{0.45}Cr_{0.55}Mn_{0.15}Ni_{2.5}Co_{1.5}Cs_{0.05}$ $K_{0.15}Na_{0.20}Ge_{0.05}O_x$+50% $SiO_2$ was obtained. Using the catalyst thus obtained, the reaction of propylene ammoxidation to acrylonitrile was conducted at the substantially same conditions as in Example 1. The results thus obtained were as follows:

The acrylonitrile yield was 81.3%. The selectivity of acrylonitrile was 81.9%. The propylene conversion was 99.1%.

Using the catalyst of the present invention, the technology for recovery and refining of acrylonitrile is the same as the conventional one. The unreacted ammonia in the effluent from the fluidized-bed reactor is removed to a neutralization tower and all the organic components are absorbed by water in an absorption tower. Extractive distillation is used for removing hydrogen cyanide and water from the absorbed liquid to obtain highly purified acrylonitrile.

Due to the fact that W in the composition B is useful for the increase of reaction load, Sb in the composition B and Sr in the composition C can improve the running performances of catalyst at high reaction pressure. Therefore, by eliminating some components which have adverse effect on the catalyst property at high pressure and high load, and taking a good consideration of relationship of element in the catalyst element, the catalyst will have running capability at higher reaction pressure (0.14 Mpa) and higher load (0.09 $hr^{-1}$). Besides, the yield of acrylonitrile also can be up to 82.3%, so a better effect can be achieved.

What is claimed is:

1. A fluidized-bed catalyst for the ammoxidation of propylene to acrylonitrile, comprising silica as a carrier wherein the silica is present in an amount of 30–70 wt. %, and a composition represented by the following general formula:

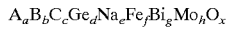

wherein
component A represents at least one element selected from the group consisting of Li, K, Rb, Cs, Sm, In and Tl;

component B represents a mixture of Pr plus W or a mixture of Pr plus W and at least one element selected from the group consisting of P, Sb, Cr, Ce, As, B, Te, Ga, Al, Nb, Tb, La and V;

component C represents at least one element selected from the group consisting of Ni, Co, Sr, Mn, Mg, Ca, Zn, Cd, Cu and mixtures thereof:

a is a nunber of from 0.01 to 1.5;

b is a number of from 0.01 to 3.0;

c is a number of from 0.1 to 12.0;

d is a number of from 0.01 to 2.0;

e is a number of from 0.01 to 0.7;

f is a number of from 0.1 to 8;

g is a number of from 0.01 to 6;

h is a number of from 12 to 14.5;

the atom value of Pr is a number of from 0.1 to 0.75;

the atom value of W is a number of from 0.1 to 1.0 and x denotes the number of oxygen atoms which satisfies the valence requirement of the other elements in the catalyst.

2. A catalyst according to claim 1, wherein component C is at least one element selected from a group consisting of Mg or the mixture of Mg with other metals.

3. A catalyst according to claim 1, wherein component B is selected from the group consisting of a mixture of Pr plus W plus Sb and a mixture of Pr plus W plus Sb with other metals, and component C is selected from the group consisting of Sr and a mixture of Sr with other metals.

4. A catalyst according to claim 1, wherein the component B is selected from the group consisting of a mixture of Pr plus W plus Ce and a mixture of Pr plus W plus Ce with other metals, and component C is selected from the group consisting of Mg and a mixture of Mg with other metals.

5. A catalyst according to claim 1, wherein component B is selected from the group consisting of Pr plus W plus Cr plus La and a mixture of Pr plus W plus Cr plus La with other metals, and component C is selected from the group consisting of Mg and a mixture of Mg with other metals.

6. A catalyst according to claim 1, wherein c is a number of from 2 to 10.

7. A catalyst according to claim 1, wherein d is a number of from 0.01 to 1.0.

8. A catalyst according to claim 1, wherein e is a number of from 0.05 to 0.5.

9. A catalyst according to claim 1, wherein f is a number of from 1.0 to 3.0.

10. A catalyst according to claim 1, wherein g is a number of from 0.1 to 2.0.

11. A catalyst according to claim 1, wherein the silica content is in the range of 40 to 60 wt. %.

* * * * *